United States Patent
Thorne, IV et al.

(10) Patent No.: US 6,773,677 B2
(45) Date of Patent: Aug. 10, 2004

(54) SLIDE CASSETTE FOR FLUIDIC INJECTION

(75) Inventors: Edward H. Thorne, IV, Milford, MA (US); George Grubner, Needham, MA (US)

(73) Assignee: Caliper Life Sciences, Inc., Mountain View, CA (US)

(*) Notice: Subject to any disclaimer, the term of this patent is extended or adjusted under 35 U.S.C. 154(b) by 0 days.

(21) Appl. No.: 10/308,552

(22) Filed: Dec. 3, 2002

(65) Prior Publication Data

US 2003/0129756 A1 Jul. 10, 2003

Related U.S. Application Data

(60) Provisional application No. 60/381,196, filed on May 17, 2002, and provisional application No. 60/347,040, filed on Jan. 9, 2002.

(51) Int. Cl.[7] ............................. C12M 1/22; B01L 3/00
(52) U.S. Cl. .................... 422/102; 422/104; 435/305.3; 435/305.4
(58) Field of Search .......................... 422/99, 103, 104; 435/288.1, 288.2, 288.4, 290.4, 305.3, 305.4

(56) References Cited

U.S. PATENT DOCUMENTS

| | | |
|---|---|---|
| 3,928,142 A | 12/1975 | Smith |
| 4,029,070 A | 6/1977 | Kobayashi |
| 4,229,920 A | 10/1980 | Lount |
| 4,847,208 A | 7/1989 | Bogen |
| 5,073,504 A | 12/1991 | Bogen |
| 5,100,626 A | 3/1992 | Levin |
| 5,192,503 A | 3/1993 | McGrath et al. |
| 5,231,029 A | 7/1993 | Wootton et al. |
| 5,273,905 A | 12/1993 | Muller et al. |
| 5,620,860 A | 4/1997 | Jacobs et al. |
| 5,830,413 A | 11/1998 | Lang et al. |
| 6,022,689 A | 2/2000 | Sarto et al. |
| 6,225,109 B1 | 5/2001 | Juncosa et al. |
| 6,258,593 B1 | 7/2001 | Schembri et al. |

Primary Examiner—Lyle A. Alexander
(74) Attorney, Agent, or Firm—Andrew L. Filler

(57) ABSTRACT

A system for holding a slide. The system includes a housing having a side wall and a top. The top includes a recess surrounded by an outer rim. The system also includes an inlet port in communication with the recess and an elevating mechanism capable of receiving the slide and for raising the slide toward the top of the housing to engage the slide with the outer rim to form an analytical cavity. Together these elements form an analytical cavity in which the assay may be performed.

37 Claims, 5 Drawing Sheets

US 6,773,677 B2

SLIDE CASSETTE FOR FLUIDIC INJECTION

CROSS REFERENCE TO RELATED APPLICATIONS

This application claims priority under 35 U.S.C. §119(e) to U.S. provisional patent application Ser. No. 60/347,040, filed Jan. 9, 2002, and provisional patent application Ser. No. 60/381,196 filed May 17, 2002.

FIELD OF THE INVENTION

This invention relates to an improved cassette for holding and applying reagents to a slide that bears samples to be assayed, and methods for use of the cassette.

SUMMARY OF THE INVENTION

An embodiment of the present invention relates to a system for holding a slide. The system includes a housing having a side wall and a top. The top includes a recess surrounded by an outer rim. The system also includes an inlet port in communication with the recess and an elevating mechanism capable of receiving the slide and for raising the slide toward the top of the housing to engage the slide with the outer rim to form an analytical cavity. Together these elements form an analytical cavity in which the assay may be performed.

BACKGROUND

Processing of biological samples on glass slides has a long history. Compared to the relatively simple dyes and stains of previous years, many newer techniques for analysis are significantly more complex and the reagents considerably more expensive. Immunoassays, hybridization assays, and in situ nucleic acid amplification assays are particularly demanding in terms of reagent expense, need for accurate timing, and need for precise temperature control. These are particularly demanding because the reagents should be applied in a precisely controlled thickness. Further, some of these assays involve heating of the slide and reagents to produce enzymatic reactions, yet the reagents must not evaporate during the procedure. In addition, it is desirable to have the assays performed automatically to whatever extent is possible, both to save cost and for increased reliability and precision.

DESCRIPTION OF THE FIGURES

For the present invention to be understood clearly and readily practiced, the present invention will be described in conjunction with the following figures, wherein.

DETAILED DESCRIPTION OF THE INVENTION

An embodiment of the present invention relates to an improved cassette for holding and applying reagents to a microscope slide that bears samples to be assayed. Generally, the cassette may be configured as a small, box-like housing having top, side, and end walls and an opening into which a slide carrying a specimen to be investigated is inserted. The term "analytical cavity," as used herein, refers to a sealed, shallow space formed between the top, side, and end walls. The term "assay" refers to either assay reagents or fluid applied to a slide that may carry analytical reagents in spots or zones that capture or react with elements of a specimen. For example, an array of nucleic acid spots can either be individual samples to be assayed with a probe or combination of probes. As another example, the array can be used to detect the presence of certain sequences in the solution in the cavity, and thus the solution is the sample. Either type of assay is accessible with the cassette of the invention. Finally, the term "analyte" refers to any material that is subject to analysis including any biological material comprising, for example, one or more of a nucleic acid, a protein including a peptide, a carbohydrate, a lipid or metabolite or other small biological molecule or biological structure such as an organelle, a cell or a tissue.

The cassette may be designed, for example, to hold the slide in a manner that creates a shallow, sealed analytical cavity over the slide surface to facilitate application and aspiration of a sequence of liquid solutions to a specimen on the slide. In that regard, the cassette may be adapted for applications involving, for example, DNA microarray hybridization, immunohistochemical staining, or any technique or procedure that involves interaction of a thin film of fluid with a lamina. The cassette may also be useful in the automated handling and processing of samples during chemical, clinical, biochemical, or molecular biological analysis or in the creation of analytical structures including, for example, a gel for electrophoresis.

Figure 1:
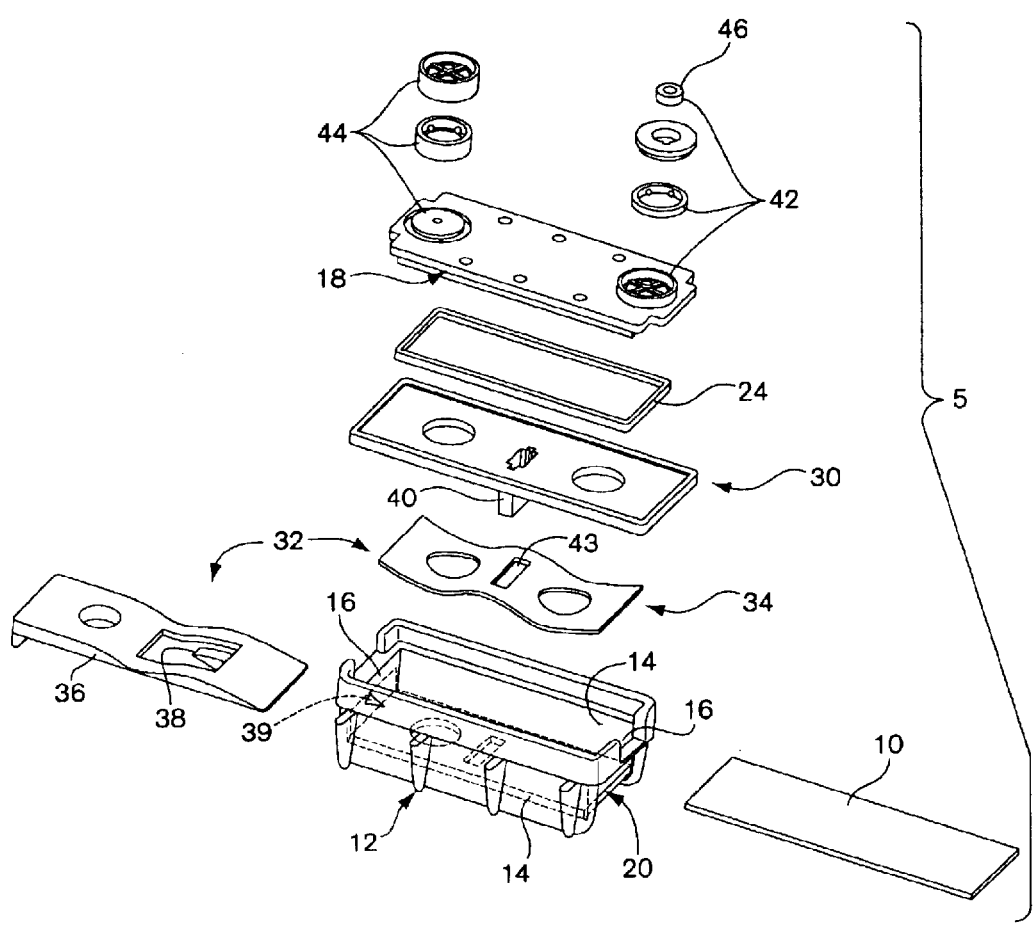
FIG. 1 is an exploded diagram that illustrates a cassette according to an embodiment of the present invention.

FIG. 1 is an exploded diagram that illustrates the basic components of a cassette 5 according to an embodiment of the present invention. As shown, cassette 5 comprises a small box-like housing 12 that includes, in large part, rectangularly arranged side walls 14 and end walls 16, a slide 10, a transparent top wall 18 (also called "lens 18"), a rectangular gasket 24, an elevator plate 30, an elevating mechanism shown generally as 32, an input port 42, and an output port 44. One of the end walls 16 may have an opening 20 through which slide 10 carrying a specimen may be inserted. Opposite end wall 16 may include a similar opening 39 through which slide 10 may be manipulated. In operation, elevating mechanism 32 raises slide 10 upwardly toward top wall 18 of housing 12 and into sealed engagement with peripheral gasket 24, thus defining a sealed, shallow analytical cavity 29 (shown in FIG. 3) between top wall 18 and slide 10, which may be approximately 0.001 to 0.002 inches deep. The shallow depth of the analytical cavity may be designed to ensure that the liquid in the chamber will be maintained at a uniform thickness and that gas bubbles will not form unless intended as a byproduct of the chemical reaction.

Lens 18 may be attached to housing 12, either during manufacture or subsequently, by permanently bond or other attachment means including, for example, gluing, welding, ultrasonic welding, stamping, crimping, press fitting, solvent bonding, brazing, affixation with fasteners, snap fitting, and similar methods as known in the art. According to another embodiment, the lens may be formed as part of the frame during its manufacture.

Lens 18 may comprise any material compatible with the assay to be performed in the cavity such as a plastic, metal, ceramic, fibrous composite, or any combinations thereof.

Lens 18 may be coated to protect the assay from the underlying material. To maintain the surface of the lens that forms the cavity in a planar fashion, lens 18 may be formed by methods that minimize the residual strain or stress in the lens material, such as sequential-compression injection molding.

Elevating mechanism 32 includes a substantially sinusoidal-shaped leaf spring 34 and a slide release 36 (also referred to as a "sliding spring lock 36"). Spring 34 is located between pressure plate 30 and slide release 36. Slide release 36 has an upper surface with a complementary shape to that of leaf spring 34. Slide release 36 may be moved into and out of housing 12 through opening 39 in end wall 16 of housing 12. Contours of leaf spring 34 and slide release 36 are formed so that when slide release 36 is pulled outwardly, an alignment interface exists between slide release 36 and spring 34, allowing spring 34 and elevator plate 30 to drop to a lowered position within substantially sinusoidal shape of slide release 36 and release slide 10. In the lowered position, cassette 5 is receptive to insertion or removal of slide 10 through aperture 20. When slide release 36 is pushed back into housing 12, a non-alignment interface exists between the release 36 and spring 34, causing elevator plate 30 to move upwardly to press slide 10 against gasket 24 and a ledge or rim 28, shown in FIG. 3, formed about the perimeter of the lens 18. Slide release 36 includes a wedge-shaped finger 38 that is engageable with an aperture on a U-shaped stirrup 40 that extends downwardly from the pressure plate 30. Stirrup 40 extends through a slot 43 in spring 34. When slide release 36 is withdrawn, finger 38 engages stirrup 40, to pull elevator plate 30 downwardly to avoid any possibility of the elevator plate becoming stuck.

According to one embodiment, lens 18 may have significant transmittance in at least one wavelength band or region of the spectrum or may otherwise be compatible with measurement of a property of the cassette or an analyte by any desired method, so that the assay can be observed, read or controlled without opening the cassette. According to another embodiment, the cassette may incorporate a viewing hole through housing 12 or alternatively through spring 34, elevator plate 30, and slide release 36, or through all of these, that will permit observation of slide 10. Any analytically useful means of observation is potentially useable with the cassette. Electromagnetic radiation of any wavelength may be used for such observation, including (but not limited to) infrared, visible and ultraviolet light.

According to another embodiment, cassette 5 may incorporate probe windows (not shown) through, for example, spring 34 and elevator plate 30 that allow the temperature of slide 10 to be measured either directly with a probe, indirectly with an infrared sensor or similar device, or other means for measuring or otherwise inferring the characteristics of the assay. Other probes of analytical cavity 29 and/or slide 10 include, without limitation, ultrasonic and other pressure waves, techniques such as fluorescence, fluorescence polarization, phosphorescence, thermoluminescence, emission or absorption of ionizing radiation, conductivity, magnetic effects, electrostatic effects, and other suitable methods for probing analytical cavity 29.

Valved inlet and outlet ports 42 and 44, which may be secured to lens 18, enable selected fluids to be admitted into and aspirated from analytical cavity 29 while minimizing evaporation of a liquid, even when cassette 5 is heated such as during an incubation period. At least one port is equipped with a one-way or check valve that may prevent bubble entrapment during exchange of reagents. Input port 42 includes, among other things, an elastic outer seal 46 that forms an airtight engagement with a cannula or similar device used to inject liquid into cassette 5. Although cassette 5 includes ports 42 and 44 on lens 18, those of ordinary skill in the art will appreciate that ports 42 and 44 may be placed in any convenient location that communicates with the interior of analytical cavity 29. Ports 42 and 44 are described in greater detail below in connection with FIG. 4.

Another embodiment of the slide release, similar in many respects to slide release 36, incorporates a ramp-like feature so that when the slide release is pulled away from housing 12, the slide release may contact the bottom of elevator plate 30 and pull elevator plate 30 downward. Pushing the slide release into housing 12 reverses this process and again forces elevator plate 30 upward, sealing analytical cavity 29 if slide 10 is present.

Although cassette 5 is equipped with spring 34, those of ordinary skill in the art will appreciate that other lift means may be suitable, including a wedge, clamp, cam, lever, or piston (or similar device driven by hydraulic or pneumatic force or electricity). Those of ordinary skill will also appreciate that the compressive force could be applied by one lift means and retained by others, such as a strip of adhesive or a pin-type interlock.

Gasket 24 can be made of any suitable material that maintains a desired degree of resilience at the temperatures and pressures of the assay, which may range from about −20 to about 100 degrees C., and generally less than about 1 bar above ambient pressure. According to an embodiment, a groove 26 is formed during the initial molding of lens 18 by insert molding (see FIG. 2). Outlet holes running through lens 18 to the bottom of groove 26 serve both as exit pathways during molding and, after the gasket material is cooled, as retainers of gasket 24. FIG. 1 illustrates these holes around the periphery of lens 18.

Cassette 5 may comprise any suitable material including, for example, plastic, metal, or any combination thereof. Metal may be used when, for example, heat is to be conducted. Any of the standard fabrication techniques may be used to make the parts, including cutting, stamping, casting, machining, press-forming, molding, and injection molding.

Figure 2:
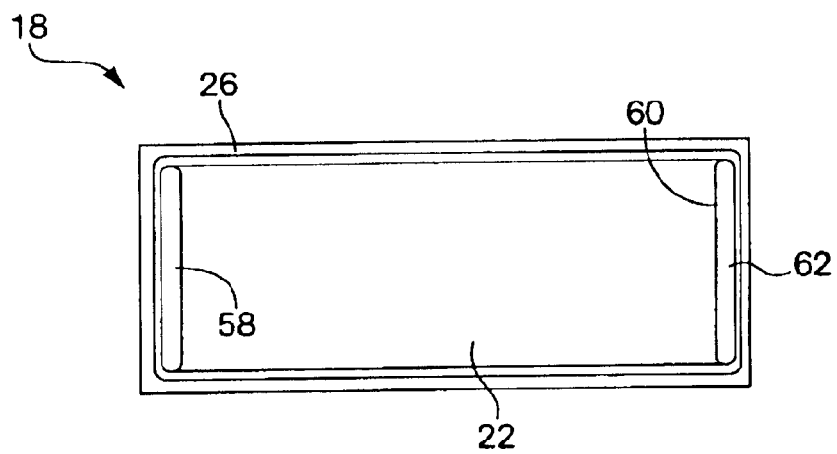
FIG. 2 is a plan view of a cassette according to an embodiment of the present invention.

FIG. 2 illustrates the underside of lens 18 according to an embodiment of the present invention. As shown, the underside of lens 18 includes a slightly recessed area 22, groove 26 formed at the margin of recessed area 22, an input channel 58, an output dam 60, and an output channel 62. Input port 42 is located to the left in FIG. 2. Groove 26 is designed to receive elastic rectangular gasket 24, either permanently or removably, so that the lower edge of gasket 24 projects downwardly beyond ledge 28 (see FIG. 3). The device may be designed so that when slide 10 is urged upwardly toward lens 18, the peripheral margin of the upper surface of slide 10 will engage ledge 28 and, in doing so, will engage and compress gasket 24, effecting a seal between the slide 10 and the gasket 24. Engagement of slide 10 with ledge 28 defines, with precision, the spacing between the upper surface of slide 10 and the underside of the lens 18 and, therefore, the depth of analytical cavity 29. The underside of the lens 18 is configured to reduce the incidence of bubbles during fluid injection.

Input channel 58 may be cut or molded into the inner surface of lens 18 to control the flow of liquid into analytical cavity 29. Liquid enters the cavity through input port 42. It first fills channel 58. As more liquid is admitted, the liquid begins to flow along and towards the opposite end of analytical cavity 29 as a uniform wave front. The wave front advances through the cavity, until it meets output dam 60, a curved narrow ridge that protrudes slightly from inner surface 22 of lens 18. Dam 60 forces the flow of the liquid towards the sides and corners of the cavity. Bubbles that otherwise might be trapped in the corners of the cavity are swept into output channel 62. Output channel 62 is tapered at the corners to facilitate the movement of liquid and bubbles to output port 44.

Figure 3:
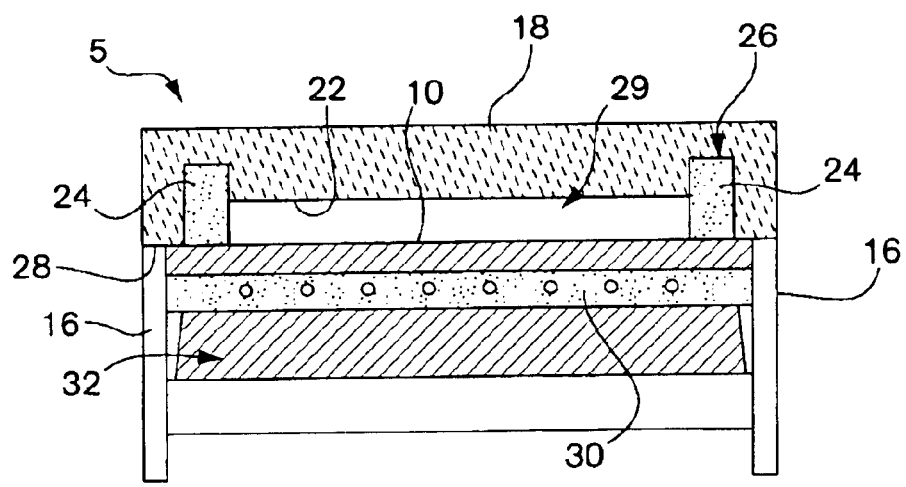
FIG. 3 shows a cross sectional view of a cassette according to an embodiment of the present invention.

FIG. 3 is a longitudinal section view of cassette 5 according to an embodiment of the present invention. Elevator plate 30 may be moved between a lower position, in which slide 10 can be placed on its upper surface when slide 10 is inserted through insert opening 20, and an elevated position in which slide 10 is pressed upwardly into engagement with the ledge 28 and into sealed relation with gasket 24. Elevator plate 30 is raised and lowered by elevating mechanism 32.

Figure 4:
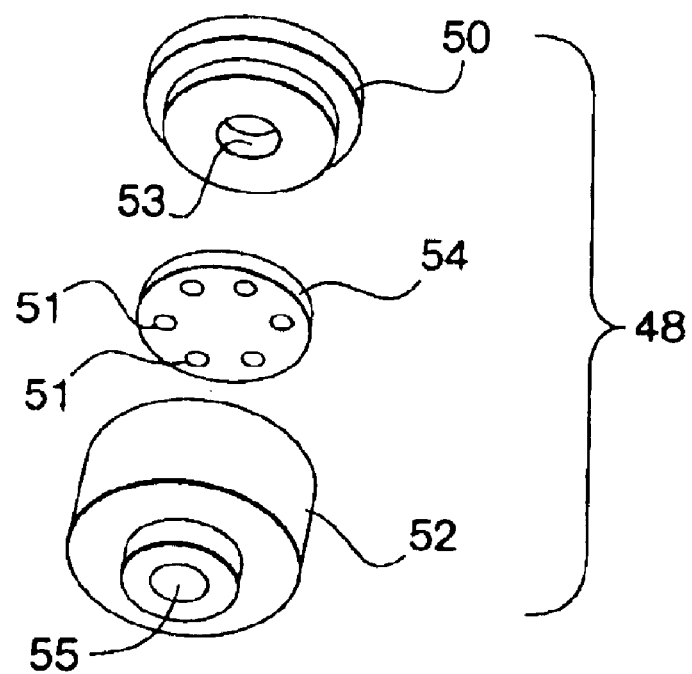
FIG. 4 is an exploded diagram of a check valve according to an embodiment of the present invention.

FIG. 4 illustrates the components of an exemplary valve assembly 48 that may be integrated into each port 42 and 44 according to an embodiment of the present invention. Valve 48 includes an input section 50, an output section 52, and an elastic septum 54. Input and output sections 50 and 52 are made of a rigid material, having little resilience at the moderate forces used in the device. The septum is fabricated from an elastic material. Septum 54 is captured and sealed about its peripheral margin between input and output sections 50 and 52 and is stretched over a convex surface of input section 50 during assembly. An inner face of output section 52 is recessed to enable septum 54 to bow sufficiently to unblock an inlet passage 53 and enable flow through a plurality of circumferential holes 51 in septum 54 and outlet passage 55 of output section 52. Reverse flow of liquid or gas (to prevent evaporation) is blocked by the central portion of septum 54 that is biased, by its inherent elasticity, against inlet passage 53. Forward flow through valve 48 begins when a sufficient pressure differential is developed across valve 48 to cause the center of septum 54 to bow away from inlet passage 53. The pressure differential may result from positive pressure of the fluid being emitted to the inlet side of valve 48 or suction applied to the outlet side. The elastic characteristic of the material of septum 54 as well as the thickness and the degree to which septum 54 is stretched determine the cracking pressure of valve 48.

The pressure differential may be, for example, between 2 and 5 psi. The upper desirable pressure limit will be determined by the degree to which slide 10 bends under the pressure or vacuum. The lower limit is indicative, to some extent, of quality of the seal because a higher backpressure can diminish reagent loss during incubation.

Valve 48 may be directly secured to lens 18 to minimize dead volume, and therefore reagent waste. According to one embodiment, positioning output section 52 very close to septum 54 may minimize dead volume. Additionally, to prevent blockages, the inner surface of output section 52 may include shallow grooves that radiate from the outlet hole, which carries fluid from the holes in septum 54 to the outlet hole. Valves 48 may be oriented to allow a flow of liquid through analytical cavity 29 from inlet to outlet so that, when an initial or a replacement reagent passes through analytical cavity 29, significant mixing will not occur.

According to an embodiment, outlet port 44 of cassette 5 may be arranged to require a greater cracking pressure than that of inlet port 42 in order to present a continuous back pressure opposing the injection of liquid into the cavity. The back pressure prevents capillary action that might otherwise result between the closely spaced surfaces of lens 18 and slide 10. If, during the liquid injection process, capillary action were permitted to draw liquid through the analytical gap, bubbles might develop within the liquid layer. The increased cracking pressure of outlet port 44 may be the result of the selection of septum thickness or material or may be provided by connecting output port 44 to an external flow restriction device.

According to an embodiment, tubing may be connected to valves 48 to supply and receive liquid. For example, a tubing attachment nipple may be included on the inlet or outlet side of valve 48 during fabrication (not shown). Alternatively, the exposed surfaces of valves 48 may be designed so that a robotic connector can mate with them and form a simple connection that is sealed by a slight force of the connector against inlet or outlet ports 42 and 44.

Figure 5:
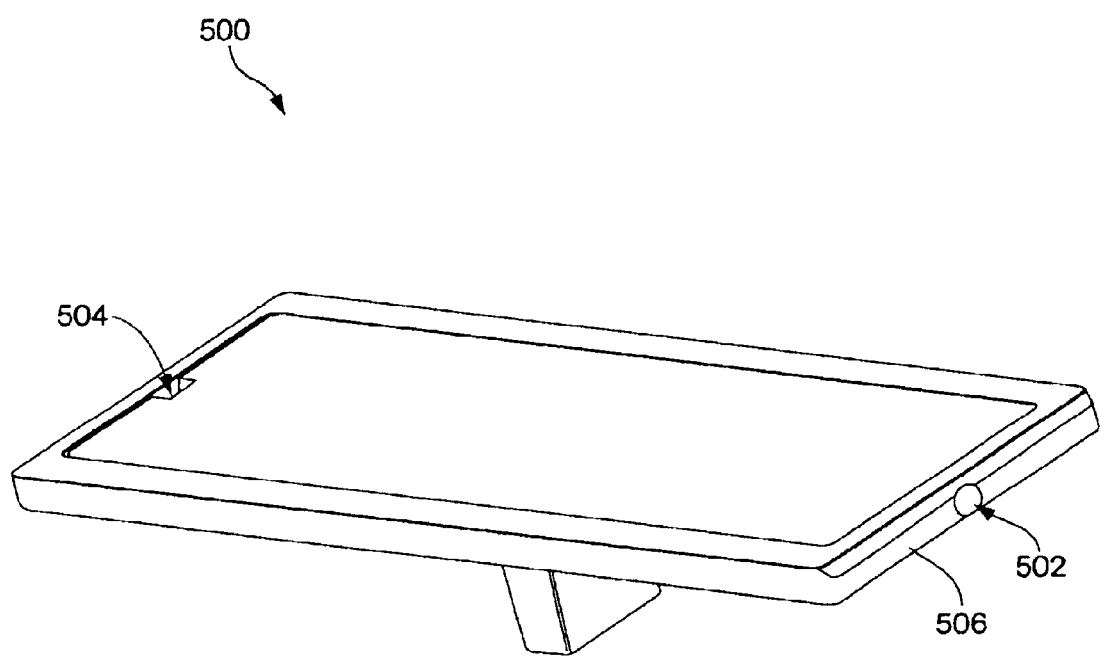
FIG. 5 is an isometric diagram of an elevator plate for heating or cooling a slide directly below the array according to an embodiment of the present invention.

FIG. 5 is an isometric diagram of an elevator plate 500 for heating or cooling a slide directly below the array according to an embodiment of the present invention. Elevator plate 500 is similar to elevator plate 30 in many respects except that elevator plate 500 includes a gas injection port 502, a gas exhaust port 504, and a beveled edge 506 that may facilitate insertion of slide 10. In operation, elevator plate 500 raises slide 10 upwardly toward top wall 18 of housing 12 against peripheral gasket 24 and rim 28, leaving a gap of approximately 0.010 inches between slide 10 and elevator plate 500. Gas injection port 502 and gas exhaust port 504 communicate with the gap so that a gas can flow beneath slide 10 for heating or cooling by either forced or natural convection. According to another embodiment, the gap between slide 10 and elevator plate 500 may be designed to accommodate liquids of various temperatures.

Variations in the height of analytical cavity 29 may create undesirable flow characteristics during the process of introducing liquids into this cavity. Chemical reactions within this cavity may often become diffusion limited, making local variations in the cavity's height important. An analytical cavity of uniform depth may contribute to uniform flow characteristics through the cavity.

During incubation, cassette 5 may be heated by direct infrared radiation or by placing a ferrous metal plate at the top of elevator 32 directly below slide 10 and using inductive heating. Alternately, slide 10 may be heated by injecting warm gas through the cavity while monitoring the temperature of slide 10 through a viewing port formed in elevator plate 30. According to another embodiment, slide 10 may be heated by placing the whole assembly in an oven or other controlled temperature space, such as for long incubations or overnight hybridization. Additionally, liquids in analytical cavity 29 may be mixed or agitated by mechanical, ultrasonic, or other mixing means to improve the quality of the reaction.

In many assays, liquids must be introduced into the cassette, incubated, removed, and, optionally rinsed. To accomplish this in a manner that is reproducible, the cassette must allow liquids to be applied to the surface of the slide in a uniform manner. In particular, application of liquids should be without the formation of gas bubbles during the application step. However, bubble formation may be a byproduct of chemical reactions between or among samples and reagents. The cassette must allow the liquid to be removed from the surface of the slide and other applications of the same or of a different liquid to be made without violating the above requirements. The removal of liquids from the cassette may be accomplished using a vacuum source, or by pressure applied to the inlet side of the cassette. According to an embodiment, the cassette may be prepared for a second liquid by flushing the first liquid with an inert liquid, such as a saline solution.

Any suitable method may be used to add liquids to analytical cavity 29 or to remove them. For example, when liquid or gas is injected into the inlet port 42 of cassette 5, the fluid pushes against septum 54, thus distorting its shape. This process opens paths for liquid or gas to flow through valve 48. Applying a vacuum to outlet port 44 produces the same result. As noted above, elastic characteristics of the septum's material and the thickness of septum 54 determine the overall backpressure of valve 48. Equivalent considerations apply to other one-way valve designs, such as the one-piece "duckbill" valve and other forms. For example, it is possible to adjust opening force by adjusting spring strength in a "poppit and spring" type of check valve, or by varying the length of the slit or the thickness of the plastic in a duckbill-type valve.

Cassette 5 of the present invention may be assembled in any suitable manner, such as by placing slide release 36 and spring 34 into housing 12, and then elevator plate 30. Independently, gasket 24 may be formed in groove 26, and valves 42, and 44 may permanently joined to the lens. Next, lens 18 may be placed into the top of housing 12 and permanently bonded thereto. Finally, cassette 5 may be package and sterilized, if required.

Figure 6:
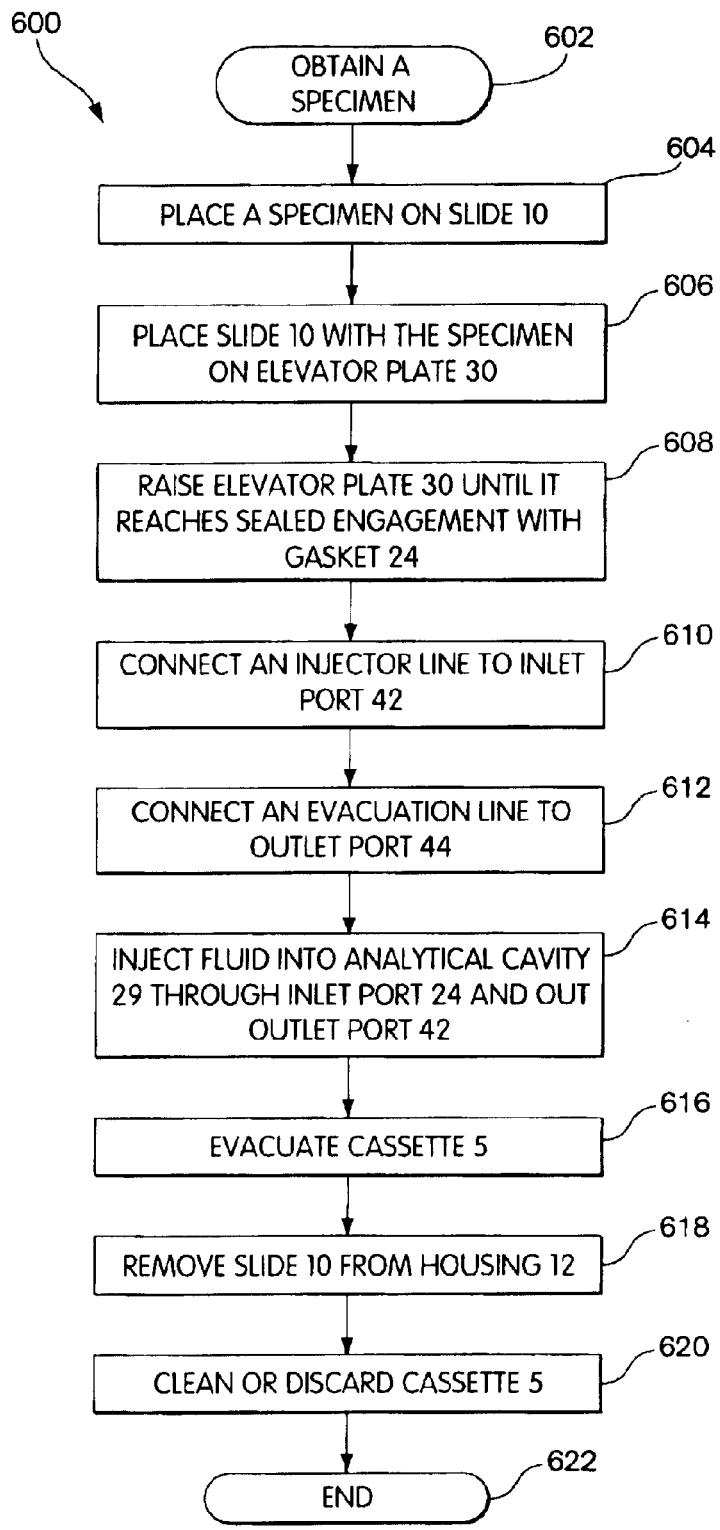
FIG. 6 is a flow diagram that illustrates an exemplary method for using a cassette in accordance with the present invention.

FIG. 6 illustrates an exemplary method 600 for using cassette 5 in accordance with the present invention. An array of spots containing DNA to be tested (step 602) is printed on a glass slide (step 604) and dried and baked sufficiently long to ensure adhesion. The slide is inserted into a cassette of the invention in step 606, and the cassette is closed in step 608. The cassette is then transported to a workstation and placed in line for processing. In the processing station, an injector and an evacuation line are pressed against the inlet and outlet ports of the cassette in steps 610 and 612.

The plate is first washed with a series of buffers to hydrate the sample and partially denature it in step 614. The evacuator evacuates the cavity for 5 seconds, and then the injector injects enough of the first wash solution to fill the cavity. This step is repeated twice, and then the cassette is incubated with the wash fluid for a preset period. The same procedure is applied with a second buffer, and then a third wash with hybridization buffer, each injected by a different injector connected to a supply of the wash solution.

Next, the cassette is evacuated in step 616, and the hybridization buffer containing the labeled probe is injected into the cassette enough to fill the cavity. The cassette is placed in a humidified incubator at 42 deg. C. (or a different temperature, depending on the particular hybridization and desired degree of stringency) for 12 to 16 hours. Humidification reduces the driving force for evaporation.

After hybridization is completed, the cassette is rinsed to be free of the probe, using 3 changes of wash buffer, i.e. with evacuation followed by filling with the more buffer. Then the cassette is cooled, and rinsed similarly with other buffers and evacuated. The cassette is dried by forcing warm dry nitrogen gas through the analytical cavity at a convenient rate, for example about 100 microliters/sec, for a time known to be long enough to dry the slide. The entire cassette, with the nitrogen retained by the backpressure-retaining valves, is placed in a dark place until later analysis is performed. The absence of oxygen and of light may be important to preserve the fluorescent probes typically used in such procedures.

Typically, the slide will be removed from the cassette in step 618 and placed directly in a standard fluorescence reader capable of reading the particular spot size and array size used in the particular assay. The cassette may be cleaned or discarded in step 620 to prevent any possibility of cross contamination with another assay, before ending process 600 in step 622.

Similar procedures can be devised for immunoassays or other assays involving proteins or carbohydrates, or other biological material including cells, tissues and organelles; and for binding assays of any sort, not necessarily biomedical. The ability of the cassette to remain sealed allows anaerobic assays to be conducted easily. Moreover, the ability to rapidly replace, reagent solutions is an advantage in many situations, including kinetic analysis. For example, the three-fold exchange rinse described above can be done in substantially less than one second, with appropriate machinery.

The precision of the thickness and humidity control inherent in these cassettes can also be useful in related assays requiring a support. For example, a thickness of 25 microns is suitable for thin layer electrophoresis, which could be conducted in these cassettes by providing for multiple sample injection ports or by providing samples in a porous material fixed to the slide, and then flowing in an electrophoretic separation medium, either of the gelling or the non-gelling type. Electrodes would be fitted into the lens specifically for this purpose. Voltage would then be applied to these electrodes for the purpose of electrophoretic separations.

The result and process would be generally similar to results obtained with "capillary" electrophoresis, as the thickness can be made to fall within the same general range. Thin electrophoretic layers below about 250 microns (0.25 mm) in thickness can be difficult to cast. Capillaries in present use are generally in the range of about 40 to about 100 microns. Therefore, as suitable range for cavity thickness in electrophoresis is in the range of about 10 to about 250 microns.

The foregoing description has been limited to a few specific embodiments of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

What is claimed is:

1. A device for holding a slide, comprising:
    a housing having a side wall and a top, the top having a recess surrounded by an outer rim;
    an inlet port in communication with the recess, the inlet port including a valve; and
    an elevating mechanism capable of receiving the slide and for raising the slide toward the top of the housing to sealingly engage the slide with the outer rim to form a sealed analytical cavity that is sealed from the ambient environment.

2. The device according to claim 1 further comprising a gasket disposed between the slide and the outer rim.

3. The device according to claim 1 wherein the outer rim limits upward movement of the slide toward the top of the housing.

4. The device according to claim 3 wherein the gasket projects downwardly beyond the outer rim such that when the slide moves towards the top of the housing the slide engages the gasket before engaging the outer rim.

5. The device according to claim 2 wherein the top of the housing includes a peripheral groove for receiving the gasket.

6. The device according to claim 1 further comprising means for attaching the top to the housing.

7. The device according to claim 1 wherein a fluid or gas is introduced into the analytical cavity through the inlet part.

8. The device according to claim 1 further comprising an outlet port in communication with the recess for aspirating a fluid or gas from the analytical cavity.

9. The device according to claim 8 wherein the top of the housing includes an output channel to facilitate a flow of the fluid from the inlet port to the outlet port.

10. The device according to claim 7 wherein the top of the housing includes an input channel capable of controlling a flow of the fluid into the analytical cavity.

11. The device according to claim 7 wherein the top of the housing includes a dam capable to redirect a flow of fluid in the analytical cavity.

12. The device according to claim 1 wherein the valve coupled to the inlet port is a check valve.

13. The device according to claim 12 wherein the valve includes an input section, an output section, and an elastic septum.

14. The device according to claim 13 wherein the input section includes a convex surface over which the elastic septum may be stretched.

15. The device according to claim 2 wherein the elevating mechanism includes means for lifting the slide into sealed engagement with the gasket.

16. The device according to claim 1 wherein the elevating mechanism includes an elevator plate, a leaf spring having a first substantially sinusoidal shape, and a slide release having a second substantially sinusoidal shape complementary to the first substantially sinusoidal shape and capable of sliding in and out of an alignment relationship with the leaf spring to cause the elevator plate to move away or toward the top of the housing.

17. The device according to claim 16 wherein the elevator plate includes a stirrup that extends through a slot in the leaf spring so that the side release engages the stirrup and pulls the elevator plate away from the top of the housing when the slide release is withdrawn.

18. The device according to claim 1 wherein the elevating mechanism includes an elevator plate and a slide release having a ramp-like profile such that when the slide release is inserted into the housing the elevator plate is forced toward the top of the housing.

19. The device according to claim 1 wherein the top of the housing comprises a lens.

20. The device according to claim 19 wherein the lens is substantially transparent.

21. The device according to claim 1 wherein the top is comprised of at least one of plastic, metal, ceramic, or fibrous composite.

22. The device according to claim 1 further comprising a viewing hole through which an assay may be observed on the slide.

23. The device according to claim 16 wherein the elevator plate includes a gas injection port and a gas exhaust port.

24. The device according to claim 23 wherein the gas injection port and the gas exhaust port are configured to allow a fluid to pass below the slide.

25. The device according to claim 16 wherein the elevator plate includes a beveled edge to facilitate slide insertion.

26. The device according to claim 1 further comprising mixing means for mixing fluids contained in the analytical cavity.

27. The device of claim 26, wherein the mixing means includes a fluctuating pressure applied to the housing.

28. The device of claim 26, wherein the mixing means includes a fluctuating pressure applied to the elevating mechanism.

29. A device for holding a microscope slide comprising:
a housing having side walls and a top, the top having a recess surrounded by an outer rim;
a gasket disposed between the slide end the outer rim;
an inlet port in communication with the recess including a valve which is capable of selectively admitting fluid or gas into the recess;
an outlet port in communication with the recess including a valve which is capable of selectively aspirating a fluid or gas from the recess; and
an elevating mechanism for raising the slide toward the top of the housing until the slide sealingly engages the gasket to the outer rim to form an analytical cavity that is sealed from the ambient environment.

30. The device according to claim 29 wherein the top of the housing includes an input channel capable of controlling a flow of liquid into the analytical cavity.

31. The device according to claim 29 wherein the top of the housing includes a dam capable of redirecting a flow of liquid into the analytical cavity.

32. The device according to claim 29 wherein the inlet valve is a check valve.

33. The device according to claim 29 wherein the elevating mechanism includes an elevator plate which includes a gas injection port and a gas exhaust port for heating or cooling the slide.

34. The device according to claim 29, wherein the inlet and outlet ports are disposed in the top of the housing.

35. A system for performing an assay on a microscope slide comprising: a housing having side walls and a top, the top having a recess surrounded by an outer rim; a gasket disposed between the slide and the outer rim; an inlet port in communication with the recess including a valve which is capable of selectively admitting a fluid or gas; an outlet port in communication with the recess including a valve which is capable of selectively aspirating the fluid or gas; an elevating mechanism for raising the slide toward the top of the housing until the slide sealingly engages the gasket to the outer rim to form an analytical cavity that is sealed from the ambient environment for performing the assay; and measurement means for measuring a characteristic of the assay performed on the slide.

36. The system according to claim 35, wherein the measurement means comprises a probe.

37. The system according to claim 36, wherein the probe includes a probe for measuring an ultrasonic wave, fluorescence, fluorescence polarization, phosphorescence, thermoluminescence, emission or absorption of ionizing radiation, conductivity, a magnetic effect, of an electrostatic effect.

* * * * *